(12) United States Patent
Samour

(10) Patent No.: US 6,495,124 B1
(45) Date of Patent: Dec. 17, 2002

(54) ANTIFUNGAL NAIL LACQUER AND METHOD USING SAME

(75) Inventor: Carlos M. Samour, Bedford, MA (US)

(73) Assignee: Macrochem Corporation, Lexington, MA (US)

( * ) Notice: Subject to any disclaimer, the term of this patent is extended or adjusted under 35 U.S.C. 154(b) by 0 days.

(21) Appl. No.: 09/503,715

(22) Filed: Feb. 14, 2000

(51) Int. Cl.$^7$ .............................. A61K 6/00; A61K 7/00; A61K 7/04
(52) U.S. Cl. ......................... 424/61; 424/401; 424/404
(58) Field of Search .................... 424/61, 400, 401, 424/404

(56) References Cited

U.S. PATENT DOCUMENTS

| | | | |
|---|---|---|---|
| 4,636,520 A | 1/1987 | Umio et al. | 514/399 |
| 4,957,730 A | 9/1990 | Bohn et al. | 424/61 |
| 5,002,938 A | 3/1991 | Wang et al. | 514/171 |
| 5,023,252 A * | 6/1991 | Hseih | 514/183 |
| 5,110,809 A | 5/1992 | Wang et al. | 514/171 |
| 5,120,530 A | 6/1992 | Ferro et al. | 424/61 |
| 5,219,877 A | 6/1993 | Shah et al. | 514/399 |
| 5,264,206 A * | 11/1993 | Bohn et al. | 424/61 |
| 5,346,692 A | 9/1994 | Wohlrab et al. | 424/61 |
| 5,391,367 A | 2/1995 | DeVincentis et al. | 424/61 |
| 5,464,610 A | 11/1995 | Hayes, Jr. et al. | 424/61 |
| 5,487,776 A | 1/1996 | Nimni | 106/18.35 |
| 5,696,105 A | 12/1997 | Hackler | 514/172 |
| 5,696,164 A * | 12/1997 | Sun et al. | 514/562 |
| 5,731,303 A | 3/1998 | Hsieh | 514/183 |

FOREIGN PATENT DOCUMENTS

WO    9939680    8/1999

OTHER PUBLICATIONS

Jean–Paul L. Marty, "Amorolfine nail lacquer: a novel formulation", J. of the European Academy of Dermatology and Venereology, 4(Suppl. 1), pp. S17–S–21 (1995).

* cited by examiner

*Primary Examiner*—Thurman K. Page
*Assistant Examiner*—S. Howard
(74) *Attorney, Agent, or Firm*—Pillsbury Winthrop LLP

(57) ABSTRACT

A nail lacquer for the treatment or prevention of fungal infections, such as, onychomycosis, includes fungicidally effective amount of ciclopirox, econazole, or other antifungal agent in a compatible film-forming lacquer vehicle which includes a water-insoluble film-forming polymer; pentadecalactone, or similar cyclic lactone compound or derivative thereof, and volatile solvent. The pentadecalactone functions as a plasticizer for the film-forming polymer and as a penetration enhancer for the antifungal agent. The composition, when applied to the nails provides a hard, clear, water-resistant film containing the antifungal agent. The compositions are used for the treatment of onychomycosis.

12 Claims, No Drawings

ANTIFUNGAL NAIL LACQUER AND METHOD USING SAME

BACKGROUND OF THE INVENTION (1). Field of Invention

This invention relates to antifungal nail lacquer compositions useful in the treatment of onychomycoses or other fungal infestations affecting toe nails or finger nails using the nail lacquer composition. More particularly, the invention relates to antifungal nail lacquers which may be applied to nails to form films from which the antifungal agent will be released and become available for nail penetration; and to the method for treating or preventing fungal infestations of animal nails by applying the antifungal composition to the infected nail or to the fungal susceptible nail.

(2). State of the Prior Art

Fungal infection of the nails, commonly referred to as onychomycosis, is most frequently caused by dermatophytes but also can be caused by molds and Candida. Mixed infections also occur. Onychomycosis includes dermatophyte infection of the nail plate and includes infection of nails by any fungus, including yeast or molds. Thus, for example, onychomycosis serves as a reservoir for dermatophytes and contributes to treatment failure and recurrence of tinea pedis.

Most common causes of tinea unguium are *Trichophyton rubrum* (most frequent), *T. mentagrophytes*, and *Epidermophyton floccusum*. Onychomycosis due to nondermatophytes is usually caused by Candida species.

Nail lacquers for the treatment of onychomycoses and similar fungal infections affecting nails (toe nails and/or finger nails) of humans, in particular, or other animals, are known. Representative examples are described in the patent literature, of which the following U.S. Pat. Nos. can be mentioned:

- 4,957,730 (1-hydroxy-2-pyridone in water-insoluble film-former);
- 5,120,530 (amorolfine in quaternary ammonium acrylic copolymer);
- 5,264,206 (tioconazole, econazole, oxiconazole, miconazole, tolnaftate, naftifine hydrochloride, in water-insoluble film-former); 5,346,692 (with urea and dibutyl phthalate plasticizer);
- 5,487,776 (griseofulvin as colloidal suspension).

Other U.S. Pat. Nos. which relate to antifungal products include, for example, 4,636,520, 5,002,938, 5,110,809, 5,219,877, 5,391,367, 5,464,610, 5,696,105.

Effectiveness of nail lacquers as a delivery vehicle for topically administering the antifungal agent amorolfine is described by Jean-Paul L. Marty, J. of the European Academy of Dermatology and Venereology, 4(Suppl. 1), pp.S17–S21 (1995). As described by the author, the film-generating solution as the lacquer base for the active principle basically consists of volatile solvent (ethanol, ethyl/butyl/methyl acetate, methylene chloride, methyl ethyl ketone, isopropanol), and a non-water-soluble polymer (methacrylic acid copolymers, vinyl polymers) which leaves a thin continuous film following evaporation of the solvent. Plasticizers (triacetin, dibutyl phthalate) impart sufficient mechanical flexibility to prevent flaking and removal.

More recently, some of the present inventors developed highly effective antifungal nail lacquer formulations which incorporated 2-n-nonyl-1,3-dioxolane or related dioxolane, dioxane and acetal compounds as skin (nail) permeation enhancers (SPE) and also, surprisingly, discovered that the SPE compounds function as plasticizers for the film-forming polymer. Thus, the nail lacquer formulation containing the dioxolane, dioxane and acetal classes of skin penetration enhancing compounds were able to be formulated without additional plasticizer while still providing clear, hard, water-resistant films exhibiting good adherence to nails and from which the antifungal agent could be readily dispensed into the affected nail. These antifungal nail compositions are disclosed in WO 99/39680, published Aug. 12, 1999.

Based on this experience, the present inventors attempted to find other penetration enhancing compounds which would also be useful in formulating antifungal lacquer compositions and capable of functioning as plasticizer for the film forming polymers of lacquer formulations. As a result, it was discovered that the skin penetration enhancing cyclic lactones and derivatives thereof, as disclosed in U.S. Pat. Nos. 5,023,252 and 5,731,303, the disclosures of which, are incorporated herein, in their entireties, also are compatible with a range of lacquer formulations containing film-forming polymer, antifungal agent and solvent. The present invention is based on this discovery.

SUMMARY OF INVENTION

The present invention provides an antifungal nail lacquer composition which will provide clear, hard, films adherent to nail surfaces.

According to the present invention there is provided a nail lacquer formulation incorporating an antifungal agent, which formulation, when applied to nails may yield a substantially clear film, for use in the treatment or prevention of fungal infestations or infections on or associated with nails.

In particular, the present invention provides a composition effective for the treatment or prevention of fungal infections of nails, comprising:

(a) at least one antifungal agent effective in the treatment or prevention of onychomycoses;

(b) a plasticizing and penetration enhancing agent selected from compounds of the following formula (I):

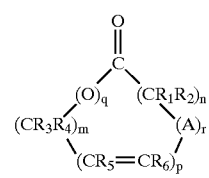

wherein
A is is group having the structure

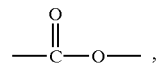

m and n are integers having a value from 1 to 20 and the sum of m+n is not greater than 25, p is an integer having a value of 0 or 1, q is an integer having a value of 0 or 1, r is an integer having a value of 0 or 1, R represents hydrogen or a straight or branched chain alkyl group having from 1 to 6 carbon atoms, and, $R_1$, $R_2$, $R_3$, $R_4$, $R_5$ and $R_6$, each, independently, represent hydrogen or a straight or branched chain alkyl group having from 1 to 6 carbon atoms, with the provisos that (i) only one of $R_1$ to $R_6$ may be said alkyl group, and
(ii) when p, q and r have a value of 0, m+n is at least 11,
(c) water-insoluble, film-forming polymer; and,
(d) volatile solvent.

The composition, when applied to nails, forms, upon evaporation of the volatile solvent, a film lacquer from which the antifungal agent is releasable and becomes available to treat or prevent fungal infection.

The invention also provides lacquer compositions effective for providing long-lasting, water-resistant adherent films on animal (e.g., human) skin and nails comprising a substantially non-aqueous solution of water-resistant, film-forming polymer, and plasticizing effective amount of at least one compound of formula (I).

The resulting water-resistant, adherent films will be suitable as a delivery matrix for drugs, including antifungal agents and others. When such film with drug incorporated therein, is deposited on animal, especially human or other mammal, skin or nail, the drug can leach from the film and be capable of being absorbed by or transported into and through the skin or nail.

DETAILED DESCRIPTION AND PREFERRED EMBODIMENTS

The present invention provides antifungal nail lacquer compositions capable of forming films which will adhere to nails upon evaporation of the volatile solvent from the film-generating solution of nail lacquer composition. These films allow diffusion of active principle(s) included in the lacquer composition from the resulting film.

The cyclic lactones and related compounds as disclosed in the aforementioned U.S. Pat. Nos. 5,023,252 and 5,731,303, are described only as enhancers for penetration of various pharmacologically active principles through the skin. The compounds of formula (I), additionally, will provide a plasticizing effect for film-forming polymers of lacquer compositions and, therefore, are sometimes referred to hereinafter as PSPE's ("plasticizing skin penetration enhancers").

The preferred PSPE's for use in the present invention are the cyclic lactones of formula (I):

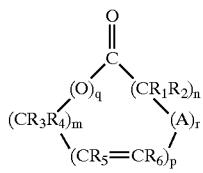

wherein
A is is group having the structure

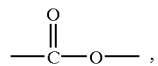

m and n are integers having a value from 1 to 20 and the sum of m+n is not greater than 25,
p is an integer having a value of 0 or 1,
q is an integer having a value of 0 or 1,
r is an integer having a value of 0 or 1,
R represents hydrogen or a straight or branched chain alkyl group having from 1 to 6 carbon atoms, and, $R_1$, $R_2$, $R_3$, $R_4$, $R_5$ and $R_6$, each, independently, represent hydrogen or a straight or branched chain alkyl group having from 1 to 6 carbon atoms, with the provisos that
(i) only one of $R_1$ to $R_6$ may be said alkyl group, and
(ii) when p, q and r have a value of 0, m+n is at least 11.

Examples of the alkyl group for R and $R_1$ to $R_6$ include methyl, ethyl, n-propyl, isopropyl, n-butyl, isobutyl, sec-butyl, amyl, hexyl, and the like.

Preferably, each of $R_1$ and $R_1$ to $R_6$ are hydrogen atoms. These preferred compounds of formula (I) are, therefore, cyclic lactones.

Another preferred class of compounds of formula (I) may be represented by the following general formula (I-A):

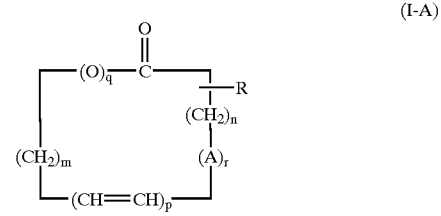

wherein X, Y, R, A, m, n, p, q and r, are as defined above.
Preferably, in formula (I-A), R is hydrogen.

The amount of enhancer compound is selected to provide the desired plasticization of the film-forming polymer and the desired delivery rate for the active compound but, taking into consideration such additional factors as, product stability, side effects, carrier system and the like. Generally, depending on the particular antifungal agent and film-forming polymer, amounts of the PSPE compound in the range of from about 0.5 to 35%, preferably from about 2 or 3 up to about 25 or 30 percent, especially from about 5 to 20 or 25 percent, most especially, from about 8 to 20% by weight of the total composition, will be compatible with the other ingredients of the lacquer composition and should provide transungal delivery of the active principle over the duration of the film on the nail. Within these ranges, the desird results (flexibility, release and skin permeation characteristics) may usually be achieved without incorporating additional co-solvents or plasticizers.

The PSPE's are, generally speaking, compatible with acrylate and methacrylate copolymers. Compatibility between the film-forming polymer and the PSPE compounds may be readily determined by one of ordinary skill in the art, such as, for example, by formation of a single homogenous phase when the polymer and PSPE are mixed together, and, more particularly, by formation of a clear film upon evaporation of solvent. As will be appreciated by those skilled in the art, various factors, such as, for example, polarity of "mer" units of the polymer, molecular weight, and the like, will be considered for compatibility.

It is expected that the plasticizing and adhesion promoting functions of the subject PSPE compounds may also be exhibited with the below-described film-forming polymers, for virtually any drug which may be dissolved in the polymer/enhancer compound matrix, with or without the assistance of solvents or co-solvents. Thus, drugs which may be topically administered to the skin as well as drugs which are adapted for use in treating nails for onychomycoses or other ailments, may be incorporated into the nail and skin-adherent polymer plus enhancer compound film-forming composition of this invention.

The film-forming polymers which may be used in the present invention are not particularly limited and may be chosen from among any of the film-forming polymers previously used in or useful for nail lacquer film-forming polymers and which are compatible with the PSPE and which have good adhesion to nail keratin (and/or skin) and form water-insoluble and/or water-resistant films which permit release of the antifungal agent and also the steroidal antiinflammatory agent, if present.

Examples of water-insoluble, film-forming polymers which may be used in the nail lacquer compositions of this invention, include, for example, polyvinyl acetate, mixed polymers (or copolymers) of vinyl acetate with acrylic or methacrylic acid, copolymers of (meth)acrylic acid and (meth)acrylate esters, copolymers of (meth)acrylic acid esters with amino group and/or quaternary ammonium group-containing comonomers, and the like. These polymers may be used alone or in mixtures with each other or with other film-forming polymers that will not impair the objectives of this invention.

As used in this application, the term "lower" in connection with "alkyl", etc., refers generally to carbon chain lengths of up to 6 carbon atoms, however, the preferred lower alkyl groups typically have from 1 to 4 carbon atoms.

Especially preferred film-forming polymers include acrylate (co)polymers, methacrylate (co)polymers, and copolymers of alkyl vinyl ether and maleic anhydride. For example, a preferred acrylic copolymer comprises recurring units of at least one of the following moieties (IV) and (V):

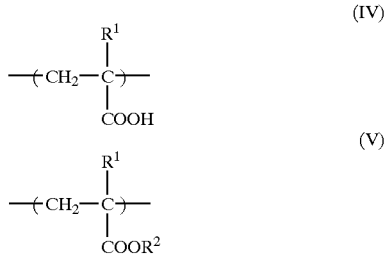

wherein $R^1$ represents H or $CH_3$; and $R^2$ represents an alkyl group of from 1 to about 12 carbon atoms, preferably from about 2 to about 12 carbon atoms, especially preferably, from about 4 to about 10 carbon atoms. The alkyl group may be linear or branched. Examples of alkyl groups for $R^2$ include methyl, ethyl, propyl, isopropyl, t-butyl, isobutyl, n-butyl, n-pentyl, 4-methyl-n-pentyl, n-hexyl, n-heptyl, n-octyl, 2-methyloctyl, n-nonyl, n-decyl, n-dodecyl, and the like.

Another useful acrylic copolymer comprises recurring units of a moiety of formula (VI)

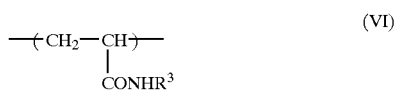

wherein $R^3$ represents an alkyl group, such as, for example, the alkyl groups described above for $R^2$; preferably an alkyl group of at least two and up to about 12 carbon atoms, especially preferably $C_4$ to $C_{10}$ alkyl.

Acrylic copolymers which comprise recurring units of formula (V) or formula (VI) or both formulas (V) and (VI), and, optionally, recurring units of formula (IV), as defined above, wherein at least one of $R^2$ and $R^3$ represents an alkyl group having at least 4 carbon atoms, are particularly preferred.

Another preferred class of acrylic copolymer comprises recurring units of acrylic and/or methacrylic acid esters and recurring units of a moiety containing a cationic amine and/or quaternary ammonium group, such as, for example, carboethoxy-t-butyl ammonium.

As is well known in the art, the cationic amine group may be quaternized by reaction of the amine with an alkylating agent or other appropriate reagent to form a salt.

For example, any of the water-insoluble quaternary ammonium group containing acrylic copolymers disclosed in the aforementioned U.S. Pat. No. 5,120,530, the disclosure of which is incorporated herein by reference thereto, may be used as the film-forming copolymer in the compositions of the present invention.

Another preferred example of the water-insoluble, film-forming polymer comprises a copolymer of alkyl vinyl ether, such as, for example, methyl vinyl ether or ethyl vinyl ether, and at least one comonomer of a monoester of a dicarboxylic acid. Examples of such comonomer of a monoester of a dicarboxylic acid are shown by the following formula (VII):

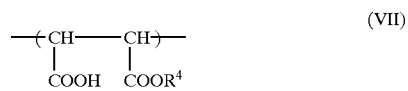

wherein $R_4$ represents a lower alkyl group, especially an alkyl group of from 1 to 4 carbon atoms, such as, for example, methyl, ethyl, propyl.

See also the film-forming polymers disclosed in the aforementioned U.S. Pat. No., 5,264,206, and the other patents mentioned above, which may also be used in this invention.

Film-forming polymers useful in the present invention are commercially available, such as, for example, the acrylic copolymers sold by National Starch Co. under the tradename DERMACRYL, e.g., DERMACRYL 79, DERMACRYL LT; the amine or quaternary ammonium group containing acrylic copolymers sold by Rohm (a division of Huls Group) under the tradename EUDRAGIT, it e.g., EUDRAGITs E, RS, RL,; the methylvinyl ether copolymers sold by ISP Corp. under the tradename GANTREZ, e.g., GANTREZ ES-3351, GANTREZ ES-425, ES-435; the quaternary ammonium acrylic copolymers sold by National Starch Co. under the tradename AMPHOMER, e.g., AMPHOMER LV-71. Particularly good results have been obtained with each of the following commercially available products:

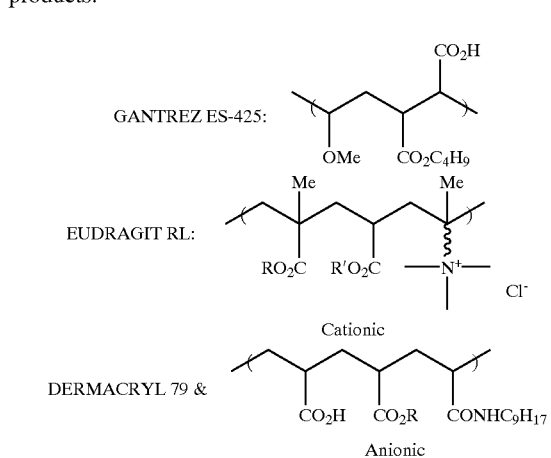

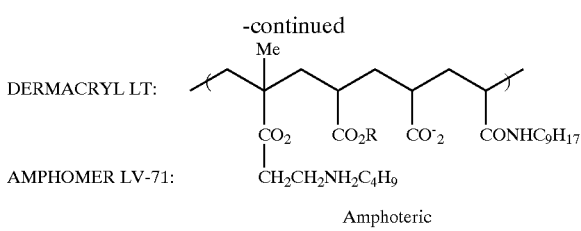

Amphoteric

The amount of film-forming polymer will depend on such factors as, for example, the molecular weight of the polymer, the desired thickness of the resulting film, the degree of water-resistance and the intended duration and delivery rate of the active agent(s), the compatibility with the other ingredients, and the like. Usually, however, satisfactory results are obtained when the amount of film-forming polymer is in the range of from about 10 to about 70 percent, preferably from about 15 to about 50 percent, especially from about 20 to 40 percent by weight of the total nail lacquer composition.

In terms of weight ratio between film-forming polymer and penetration enhancing and plasticizing compound of formula (I), suitable values of polymer:enhancer/plasticizer generally-range from about 4:1 to about 1:1, preferably from about 3:1 to about 1.2:1, especially preferably from about 2:1 to about 1.2:1. The plasticizing function of the compounds of formula (I) is exhibited over generally the same or somewhat higher concentrations as the skin penetration enhancing function. Therefore, when other plasticizing additives, as described below, are included in the compositions of this invention, the ratio of polymer to enhancer may be somewhat higher than the above ranges, for example, from about 5:1 to about 1:1.

Conventional plasticizers compatible (e.g., forming a homogenous solution and clear films) with film-forming polymers may be included in the compositions of this invention to provide additional flexibility to the dried polymer film upon evaporation of the solvent, and/or additional releasability of the antifungal agent as well as for the PSPE compound. Suitable plasticizers include, for example, 1,2,3-propanetriol triacetate (triacetin), dibutyl phthalate, dioctyl phthalate, dibutoxy ethyl phthalate, diamyl phthalate, sucrose acetate isobutyrate, butyl acetyl ricinoleate, butyl stearate, triethyl citrate, dibutyl tartrate, polyethylene glycol, dipropylene glycol, polypropylene glycols, propylene glycol, glycol fatty acid esters, such as, propylene glycol dipelargonate, and the like.

Particularly preferred plasticizers are glycols, such as propylene glycol and dipropylene glycol, glycol esters, phthalate esters, citrate esters, polyethylene glycols, and polypropylene glycols.

The type and amount of additional plasticizer, when present in the formulation, affects resistance of the dried polymer film to water and may also affect the release rate of the active drug ingredients as well as that of the PSPE compound. Those skilled in the art will recognize that the degree of water resistance can also be controlled by the type and amount of the plasticizer(s), the nature of the active principles, the choice of polymer (e.g., amount of acid groups in the polymer, etc.), the amount of the polymer, and the like.

When additional plasticizer is present it will generally be used in amounts which depend on the types and amounts of the film-forming polymer and the PSPE, most usually in the range of from about 0.5 to about 20 percent, preferably from about 2 to 10 percent, especially, from about 4 to 8 percent, based on the total weight of the composition.

While additional plasticizers may be incorporated in the invention compositions, as noted above, sufficient flexibility and adhesion, as well as compatibility (both wet and dry) between the respective ingredients, will usually be achieved without the addition of conventional plasticizers.

Solvents which may be used in the nail lacquer compositions of this invention are also not particularly critical but may be selected from among the usual physiologically safe organic solvents for lacquer compositions, so long as the active principles and film-forming polymers are soluble therein and so long as the lacquer is easy to apply and sufficiently volatile to provide acceptable drying times, usually dry to the touch in less than about 5 minutes, preferably less than about 2 minutes. As examples of such solvents mention may be made of lower alkanols, e.g., ethanol, propanol, isopropanol, butanol, isobutanol; lower alkyl esters of lower carboxylic acids, e.g., ethyl acetate, propyl acetate, n-butyl acetate, n-amyl acetate; lower alkyl ethers, e.g., methyl ether, methyl ethyl ether; lower alkyl ketones, e.g., methyl ethyl ketone; halogenated hydrocarbons, e.g., methylene chloride, methyl chloroform; aromatic hydrocarbons, e.g., toluene; cyclic ethers, such as, tetrahydrofuran, 1,4-dioxane; and mixtures thereof. Anhydrous ethanol (EtOH) is especially preferred.

The solvents used in the nail lacquer formulations of this invention are generally and preferably non-aqueous. However, in some cases small amounts of water, generally less than about 10%, preferably less than about 5% by weight of total solvents, may be used if not substantially impairing the homogeneity, clarity and solubility of the various ingredients in the lacquer solution. For example, ethanol when used may sometimes be added in the form of a 95% ethanol solution.

Again, in view of the good compatibility between the film-forming polymer and the enhancer/plasticizer compounds of formula (I), use of co-solvents, such as propylene glycol, in addition to solvent, e.g., ethanol, are usually not required and, therefore, may be omitted.

On the other hand, however, it may be desirable and, in some cases, preferred, to decrease the water-resistance of the dried polymer film, for example, to facilitate removal of the film after release of all or most of the active ingredients. Thus, in addition to a lacquer film from which the active ingredients are released over periods of several days to about 1 week or longer, lacquer films from which the active ingredient is at least substantially released over shorter periods of time, such as one day, may be desirable since many individuals are accustomed to and prefer treatments requiring applications of a drug on a daily basis.

Techniques for increasing the availability of the active ingredients for transungual delivery have been described above. When the release rate of active ingredient becomes low the film may be removed by application of suitable solvents, such as those described above, e.g., alcohols, acetone, ketones, etc., and/or by scraping or brushing, as also well known in the nail lacquer art.

Often, mixtures of volatile solvents of different boiling points, usually a low boiling solvent in the range of from about 40° C. to about 100° C. with a medium boiling solvent (boiling point up to about 150° C.) may be selected to provide drying times of no more than a few minutes or less, with uniform evaporation rates, good flow and viscosity characteristics and other desirable lacquer parameters, as well known in the cosmetic art. In some cases, high boiling point solvents, such as, for example, cellosolve, butylcellosolve acetate, butyl cellosolve, ethyl cellosolve, and the like, may be added in small amounts provided they do not impede the fast drying property and other desired characteristics.

In this connection, in its preferred embodiment, all of the volatile and non-volatile ingredients are compatible with each other and form upon mixing clear solutions which are stable against phase separation over a wide temperature range above and below room temperature, such as, for example, from temperatures within the range of from about −10° C. to about +135° C.

Another important characteristic of commmercially acceptable products is that the films formed upon evaporation of the solvent(s) and any other volatile components are strongly adherent to the nail and are water-resistant, namely, capable of withstanding repeated normal washing with soapy water for at least 1 day, usually up to about 5 or more days, preferably, at least one week, depending on the amount of antifungal agent in the film and upon the release rate of the active principles from the film. In addition, the dry films, for cosmetic appearance, should be substantially clear and transparent.

It is also within the scope of the invention to include colorants, such as pigments and/or dyestuffs, nacreous agents, pearlescent agents, fillers, and the like, to cover the nail, for example, to hide any unsightly manifestations of the fungal, yeast or other infection, or otherwise as may be cosmetically desirable.

Other conventional additives customarily present in cosmetic or medicinal nail lacquers may be included in the present formulations in their usual amounts so long as they do not interfere with the diffusion of the active principles and other parameters of the lacquer composition and dried polymer-film. Examples of such additives include, sedimentation retarders, chelating agents, antioxidants, silicates, aroma substances, wetting agents, lanolin derivatives, light stabilizers, antibacterial substances, and the like.

The lacquer compositions of this invention, with or without antifungal agent, may be prepared following any of the procedures normally employed in the nail lacquer field, noting that most of the ingredients are added as mobile liquids such that normal mixing techniques are available, with no particular order of addition of the respective ingredients being required. Generally, however, the polymer film-former, if in powder form, should be added gradually to some or all of the liquid components in such manner as to avoid clumping and resulting protracted dissolution times. Other ingredients may be added as convenient, as will be readily apparent to the practitioner.

The antifungal agent films obtained from the nail lacquers of this invention should be effective in treating onychomycoses and other fungal infections. Usually, repeated applications of the antifungal lacquer will be made over a period of several weeks to several months, depending on the severity of the infection, the amount of active agent, and the condition of the nails of the patient. The antifungal agent containing film will contain sufficient active principle to be diffused through the nail over a period of at least 1 day, and up to about 7 days. Since the film will remain in place usually for the entire period of diffusion, applications of the antifungal nail lacquer need be repeated only about once per day to about once per week. For example, it may be desired to provide formulations for daily application during the initial period of usage until the patient observes substantial reduction in the degree and extent of infection and thereafter to provide different formulations designed for less frequent applications, such as every other day, weekly, etc.

In addition to treating an existing infection or fungal infestation, the nail lacquers of this invention may also be applied prophylactically to the nails of a healthy individual who is or who believes he or she may be at risk for a mycotic infection, as a result, for example, of occupation, geographical location or otherwise. The manner of use is otherwise identical to the use in treating an existing infection, however, smaller dosages, but still at least above the MIC of the antifungal agent, may be sufficient in many cases to prevent the onset of fungal infection in the event of fungal contamination or infestation.

There is no particular limitation on the antifungal agents used in the compositions of this invention; any of the agents known to be effective for this purpose may be used and a listing of such compounds may be found, for example, in any current edition of The Merck Index under the headings "Antifungal (Antibiotic)" and "Antifungal (Synthetic)" in the Therapeutic Category and Biological Activity Index section.

As examples of suitable antifungal agents mention may be made of, for example, polyenes, e.g., Natamycin, Nystatin; allylamines, e.g., Naftifine, Terbinafine; imidazoles, e.g., Bifonazole, Chlotrimazole, Econazole, Fenticonazole, Ketocanazole, Miconazole, Oxiconazole; triazoles, e.g., Fluconazole, Itraconazole, Terconazole; tolnaftate, ciclopirox, undecylenic acid, sulbentine, and morpholines, e.g., amorolfine, and the related morpholines disclosed in the aforementioned U.S. Pat. No. 5,120,530. The 1-hydroxy-2-pyridone compounds disclosed in U.S. Pat. No. 4,957,730, the disclosure of which is incorporated herein, by reference thereto, may also be used, as may the antifungal agents disclosed in any of the other patent documents discussed in the Background of the Invention.

In the present invention, the antifungal agents are, preferably, present in the free form, e.g., as acid or base, rather than in the form of their salts. In this regard, the free form of antifungal agent will usually have a higher diffusion rate through the nail than a salt of the same agent; or, the salt form of a drug may impair the water-resistance of the lacquer film.

The amount of the active antifungal agent or mixture of such agents in the composition will depend on such factors as its structure and antimicrobial activity, release rate from the polymer film, diffusion characteristics and penetration behavior in the nail. Generally, any amount effective to kill the infecting microorganism, which will generally be several to several tens to hundreds of times greater than the Mean Inhibitory Concentration (MIC), may be included in the nail lacquer (as applied) composition.

Typically, amounts of active antifungal agent in the range of from about 0.5 to 20 percent by weight, preferably from about 1 to 10 percent, by weight, of the total composition (including solvents, film-forming polymer, enhancer, etc.) will suffice for compositions for treatment as well as compositions for prevention. The amount of antifungal agent in the dried film will, therefore, depend on the amount of agent in the lacquer solution and by the thickness of the applied film. The thickness of the film can be controlled by, for example, controlling the viscosity of the lacquer solution, such as by the type and amount of polymer, types and amounts of solvents, etc.

Conversely, on the basis of the non-volatile components of the composition, the amount of active agent is generally about 1 to 50%, preferably about 2 to 35%, more preferably, from about 2 to 30%, especially preferably from about 5 to 20%, by weight of the composition (film-forming polymer (s), active(s), PSPE, additional plasticizer(s) and other non-volatile additives).

The antifungal nail lacquers according to this invention, by virtue of the incorporation of the penetration enhancer-plasticizer, as described above, may provide therapeutically effective concentrations of antifungal agent deep into the nail bed. The minimum value of the therapeutically effective amount of antifungal agent will depend on several factors, primarily the particular antifungal agent and the degree and severity and cause of onychomycoses or other fungal infection.

Generally concentrations of antifungal agent greater than at least about 150 ppm in deep nail bed should be reached to attain favorable clinical results.

The following examples illustrate the compatability of various compositions containing pentadecalactone, as a representative compound of formula (I) but the present invention is not intended to and should not be construed to in any manner to be limited to the compositions shown in these examples.

EXAMPLES 1–8

The nail lacquer compositions shown in the following Table were prepared. Each nail lacquer composition was applied to a glass substrate and allowed to dry in air for several hours and the state (homogeneity) of the dried lacquer films were observed. Visualization of crystals was by means of videomicrographs taken under crossed polarizers. The results are also reported in the following Table. Pentadecalactone used in these examples has the following structure:

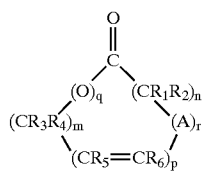

| Ingredient | Ex. 1 | Ex. 2 | Ex. 3 | Ex. 4 | Ex. 5 | Ex. 6 | Ex. 7 | Ex. 8 |
|---|---|---|---|---|---|---|---|---|
| Ciclopirox | 8 | 8 | 8 | 8 | 8 | 8 | 8 | 8 |
| Pentadecalactone | 10 | 15 | 10 | 15 | 10 | 10 | 15 | 15 |
| EUDRAGIT ® RL[a] | — | — | — | — | 25 | — | 25 | — |
| EUDRAGIT ® L[b] | — | — | — | — | — | 25 | — | 25 |
| DERMACRYL ® LT[c] | 25 | 25 | — | — | — | — | — | — |
| Ethanol | 55 | 52 | 57 | 52 | 57 | 57 | 52 | 52 |
| Appearance | clear | clear | clear | clear | cloudy | clear | crystals | cloudy |

[a]Cationic Acrylic Polymer
[b]Anionic acrylic polymer
[c]Amphoteric acrylic polymer

I claim:

1. A composition effective for the treatment or inhibiting of fungal infections of nails, comprising:

(a) at least one antifungal agent effective in the treatment or prevention of onychomycoses;

(b) a plasticizing and penetration enhancing effective amount of a compound of the following formula (I):

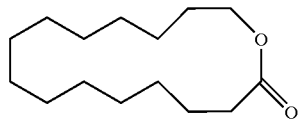

A is [is] a group having the structure

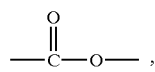

m and n are integers having a value from 1 to 20 and the sum of m+n is not greater than 25,
   p is an integer having a value of 0 or 1,
   q is an integer having a value of 0 or 1,
   r is an integer having a value of 0 or 1,
   R represents hydrogen or a straight or branched chain alkyl group having from 1 to 6 carbon atoms, and,
   $R_1$, $R_2$, $R_3$, $R_4$, $R_5$ and $R_6$, each, independently, represent hydrogen or a straight or branched chain alkyl group having from 1 to 6 carbon atoms, with the proviso that only one R1 to $R_6$ may be said alkyl group, and with the further proviso that,
   when p, q and r have a value of 0, m+n is at least 11;

(c) water-insoluble, film-forming polymer; and,
   (d) volatile solvent;
the composition, when applied to nails, forming, upon evaporation of the volatile solvent, a hard, water-resistant film from which the antifungal agent is releasable and becomes available to treat or prevent fungal infection.

2. The composition of claim 1 wherein the antifungal agent is selected from the group consisting of polyenes, allylamines, imidazoles, triazoles, ciclopirox, undecylenic acid, and amorolfine.

3. The composition of claim 1 wherein the antifungal agent comprises at least one of amorolfine, ciclopirox and econazole.

4. The composition of claim 1 wherein the antifungal agent comprises ciclopirox.

5. The composition of claim 1 wherein the antifungal agent comprises econazole.

6. The composition of claim 1 wherein the film-forming polymer comprises a water-insoluble film-forming-polymer selected from the group consisting of acrylate polymers, methacrylate polymers, and copolymers of alkyl vinyl ether and maleic anhydride.

7. The composition of claim 1 wherein the film-forming polymer comprises an acrylic copolymer.

8. The composition of claim 1 wherein the compound of formula (I) comprises pentadecalactone.

9. The composition of claim 1 which comprises:

from about 0.5 to about 20 percent (a) antifungal agent;

from about 0.5 to about 35 percent (b) compound of formula (I);

from about 0.5 to about 40 percent (c) film-forming polymer; and from about 10 to about 70 percent (d) volatile solvent.

10. The composition of claim 9 wherein the compound of formula (I) comprises pentadecalactone.

11. A method for the treatment of a fungal infection which comprises applying to an infected nail a nail lacquer composition as defined in claim 1.

12. A method for preventing a fungal infection from developing which comprises applying to the nail of a person in need thereof a nail lacquer composition as defined in claim 1.

* * * * *